United States Patent
Kramer et al.

(10) Patent No.: US 8,845,576 B2
(45) Date of Patent: Sep. 30, 2014

(54) ELECTROSURGICAL TOOL

(75) Inventors: Steven C. Kramer, San Jose, CA (US); Andrew J. Hamel, San Mateo, CA (US); Reid Cover, Mountain View, CA (US)

(73) Assignee: Stryker Corporation, Kalamazoo, MI (US)

( * ) Notice: Subject to any disclaimer, the term of this patent is extended or adjusted under 35 U.S.C. 154(b) by 778 days.

(21) Appl. No.: 12/653,841

(22) Filed: Dec. 18, 2009

(65) Prior Publication Data
US 2010/0160910 A1    Jun. 24, 2010

Related U.S. Application Data

(60) Provisional application No. 61/203,472, filed on Dec. 23, 2008.

(51) Int. Cl.
| | | |
|---|---|---|
| *A61M 1/00* | (2006.01) | |
| *A61B 18/14* | (2006.01) | |
| *A61B 18/18* | (2006.01) | |
| *A61F 7/12* | (2006.01) | |
| *A61B 18/00* | (2006.01) | |
| *A61B 17/00* | (2006.01) | |
| *A61B 18/16* | (2006.01) | |

(52) U.S. Cl.
CPC ... *A61B 18/1482* (2013.01); *A61B 2018/00601* (2013.01); *A61B 2017/00973* (2013.01); *A61B 2018/00577* (2013.01); *A61B 18/16* (2013.01); *A61B 2218/007* (2013.01)
USPC ............... 604/35; 606/41; 607/113

(58) Field of Classification Search
USPC .................. 604/35, 114; 606/32, 41, 45–50; 607/99, 105, 113
See application file for complete search history.

(56) References Cited

U.S. PATENT DOCUMENTS

| | | |
|---|---|---|
| 3,974,833 A | 8/1976 | Durden, III |
| 5,290,282 A | 3/1994 | Casscells |
| 5,324,254 A | 6/1994 | Phillips |
| 5,395,312 A | 3/1995 | Desai |
| 5,401,274 A | 3/1995 | Kusunoki |
| 5,520,685 A | 5/1996 | Wojciechowicz |
| 5,697,281 A | 12/1997 | Eggers et al. |
| 5,697,536 A | 12/1997 | Eggers et al. |
| 5,730,742 A | 3/1998 | Wojciechowicz |
| 5,810,806 A | 9/1998 | Ritchart et al. |
| 5,830,214 A | 11/1998 | Flom et al. |
| 5,833,689 A | 11/1998 | Long |

(Continued)

OTHER PUBLICATIONS

Stryker 90-ASD Probe discussed in paragraphs [0004] and [0005] of US 2006/0235377 A1 (date unknown), 2 pages.

(Continued)

*Primary Examiner* — Linda Dvorak
*Assistant Examiner* — Brian M Antiskay
(74) *Attorney, Agent, or Firm* — Flynn, Thiel, Boutell & Tanis, P.C.

(57) ABSTRACT

An electrosurgical tool for cauterizing or ablating patient tissue, which tool includes a tubular shaft which defines therein a conduit in communication with a suction source and which mounts an electrode at the distal end thereof. An electrode support element is provided at the distal end of the shaft for mounting and insulating the electrode. The support element and the electrode together define a suction opening at the treating surface of the electrode which minimizes clogging of the tool.

23 Claims, 10 Drawing Sheets

(56) References Cited

U.S. PATENT DOCUMENTS

| | | | |
|---|---|---|---|
| 5,843,019 A | 12/1998 | Eggers et al. | |
| 6,063,081 A | 5/2000 | Mulier et al. | |
| 6,102,046 A | 8/2000 | Weinstein et al. | |
| 6,156,036 A | 12/2000 | Sussman et al. | |
| 6,190,381 B1 | 2/2001 | Olsen et al. | |
| 6,214,003 B1 * | 4/2001 | Morgan et al. | 606/50 |
| 6,254,600 B1 | 7/2001 | Willink et al. | |
| 6,296,638 B1 | 10/2001 | Davison et al. | |
| 6,355,032 B1 | 3/2002 | Hovda et al. | |
| 6,379,350 B1 * | 4/2002 | Sharkey et al. | 606/41 |
| 6,406,476 B1 | 6/2002 | Kirwan et al. | |
| 6,458,126 B1 | 10/2002 | Doyle | |
| 6,461,357 B1 | 10/2002 | Sharkey et al. | |
| 6,482,201 B1 | 11/2002 | Olsen et al. | |
| 6,482,202 B1 | 11/2002 | Goble et al. | |
| 6,632,193 B1 | 10/2003 | Davison et al. | |
| 6,695,839 B2 | 2/2004 | Sharkey et al. | |
| 6,764,487 B2 | 7/2004 | Mulier et al. | |
| 6,893,442 B2 | 5/2005 | Whayne | |
| 7,241,293 B2 | 7/2007 | Davison | |
| 7,244,256 B2 | 7/2007 | DeCesare et al. | |
| 7,435,247 B2 | 10/2008 | Woloszko et al. | |
| 7,563,261 B2 | 7/2009 | Carmel et al. | |
| 7,632,267 B2 | 12/2009 | Dahla | |
| 2003/0181904 A1 | 9/2003 | Levine et al. | |
| 2005/0288665 A1 | 12/2005 | Woloszko | |
| 2006/0036237 A1 | 2/2006 | Davison et al. | |
| 2006/0106379 A1 | 5/2006 | O'Brien et al. | |
| 2006/0235377 A1 | 10/2006 | Earley et al. | |
| 2008/0234673 A1 | 9/2008 | Marion et al. | |
| 2008/0243117 A1 | 10/2008 | Sharps et al. | |

OTHER PUBLICATIONS

TriStar 50 and 50 ICW probes—ArthroCare Sports Medicine, date unknown (2 sheets).

MultiVac 50, XL, Super MultiVac 50, IFS, Super MultiVac 50 ICW probes—ArthroCare Sports Medicine, date unknown (3 sheets).

Arthrocare MultiVac 50 photo, date unknown, (1 sheet).

DiamondVac 90—ArthroCare Sports Medicine, date unknown (1 sheet).

Arthrocare Adds DiamondVac to Arthroscopy Product Line; Device Combines High Volume Suction With Aggressive Ablation, Oct. 18, 2001 (2 sheets).

TurboVac 90 ICW probe—ArthroCare Sports Medicine, date unknown (1 sheet).

CoVac 50, 50 ICW, 70 ICW and 70 probes—ArthroCare Sports Medicine, date unknown (4 sheets).

* cited by examiner

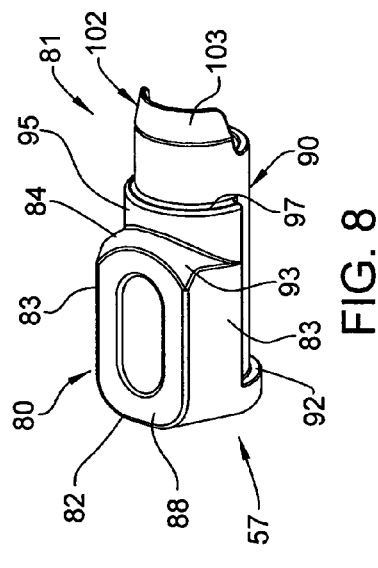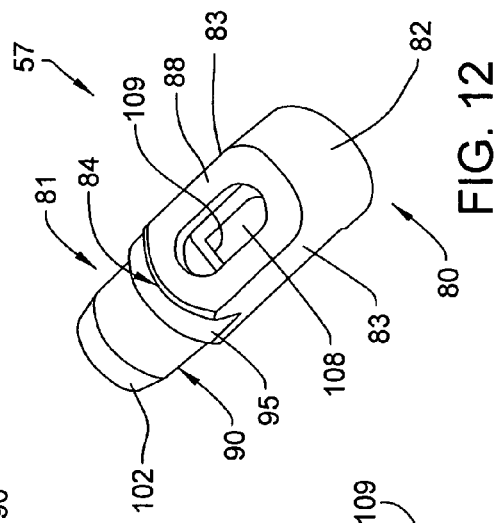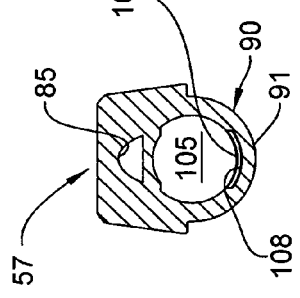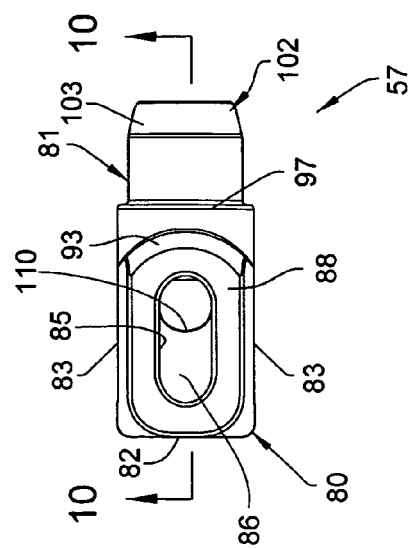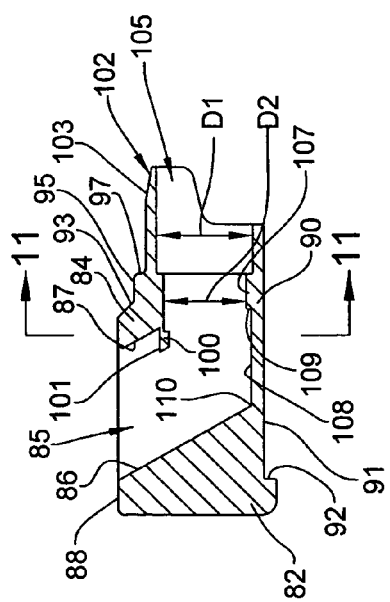

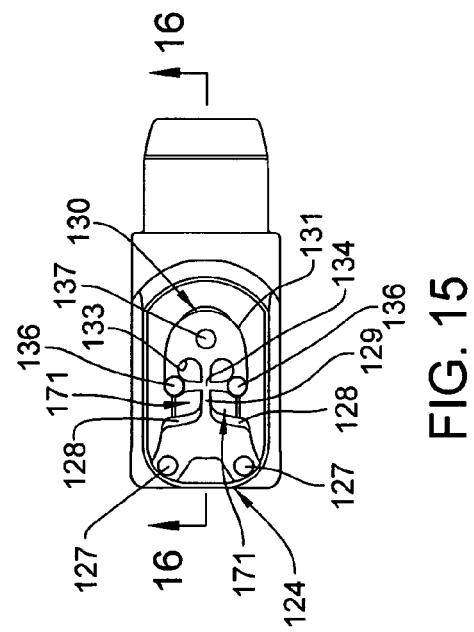
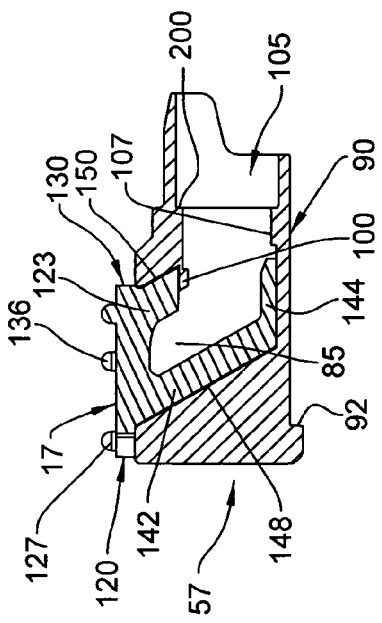
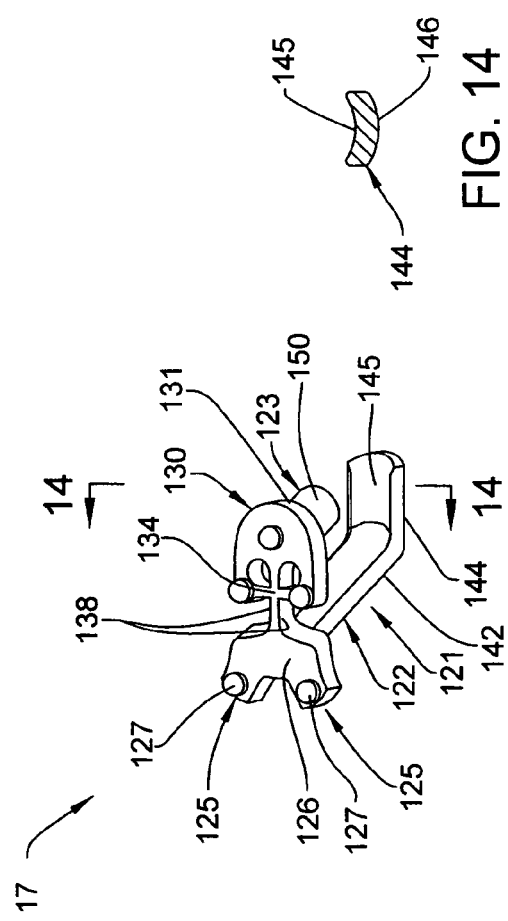
FIG. 15
FIG. 16
FIG. 14
FIG. 13

ELECTROSURGICAL TOOL

This application claims the benefit of U.S. Provisional Application No. 61/203,472, filed Dec. 23, 2008, the disclosure of which is incorporated herein by reference in its entirety.

FIELD OF THE INVENTION

This invention generally relates to an electrosurgical tool for ablation and coagulation of body tissues during surgery, and specifically to an electrosurgical tool which additionally provides aspiration or suction at the tip of the tool.

BACKGROUND OF THE INVENTION

Electrosurgical tools have been available for many years which employ electrical energy to treat targeted patient tissue in various ways. For example, electrocauterization is utilized to seal off and close blood vessels during surgery to prevent blood loss. In addition, ablation is utilized to vaporize or remove tissue using electrical energy. Electrosurgical probes are typically designed to perform both of these functions, depending upon the type of power supplied thereto. Further, monopolar and bipolar electrosurgical tools have long been available, wherein monopolar tools direct electric current from an active electrode defined on the tool through the patient's body and to a return electrode, which return electrode is typically defined by a grounding pad attached to the patient. Bipolar tools, on the other hand, incorporate both an active and a return electrode directly into the tool.

Surgical procedures utilizing bipolar tools are often performed using a conductive irrigant, such as saline, for irrigation and for distending a joint, for example in orthopedic arthroscopic procedures. The conductivity of the saline solution provides a conduction pathway between the active and return electrodes of the tool. The delivery of a high-frequency current between the active and return electrodes effectively modifies tissue, and it is common for bubbles to form on the surface of the tool or probe tip which can interfere with the surgeon's view of the surgical site. This is particularly a problem when the electrosurgical tool is employed in an endoscopic surgical procedure, wherein the tool is inserted into the surgical site through a small opening or portal formed in the patient's body. The surgeon views the surgical site through an endoscope which is inserted into the surgical site through another portal. Thus, these bubbles are generated in the relatively small confines of the surgical site and cause significant problems for the surgeon in viewing the surgical site. Further, the bubbles are electrically and thermally insulating, and can inhibit the flow of new saline solution for rewetting the electrode. Consequently, the bubbles can cause undesirable reduction of current flow through the targeted tissue.

In order to address the undesirable bubble generation described above, and also so as to allow the ability to remove treated tissue and other debris from the surgical site, some electrosurgical tools incorporate a suction feature. One type of electrosurgical tool manufactured by the Assignee hereof includes an outer conductive shaft which is covered with an insulating material. The distal end of the shaft is exposed from the insulating material, and serves as a return electrode. The active electrode is supported at the shaft tip by an insulator cap, typically constructed of ceramic. The insulator cap is mounted within the open distal end of the shaft, and defines therein two bores. The distal end of the active electrode extends through one of these bores, and a plastic suction tube extends inside and along the outer shaft and into the other bore. This arrangement thus permits a vacuum to be drawn through the tool from the distal end thereof.

Minimally invasive surgical techniques require surgical tools to be as small as possible in order to minimize trauma to the patient. As such, there is an ongoing effort to reduce the size of surgical instruments whenever possible. While the above tool works reasonably well for its intended purpose, the requirement for the outer shaft to house both a suction tube and wiring for delivering current to the active electrode can present difficulties in assembly of the tool. Further, this arrangement results in limited available space within the outer shaft, which places a limit on the diameter of a suction tube. In an effort to effectively reduce the overall size of the electrosurgical tool and simplify assembly thereof, the Assignee hereof integrated the functions of suction and energy delivery to the active electrode into one component of the electrosurgical tool. Such a tool is disclosed in U.S. Patent Publication No. US2006/0235377. This tool incorporates an electrically conductive inner shaft which defines both a suction path though the tool and an energy-delivery path to the electrode located at the distal end of the tool, which eliminates the need for wiring extending through the tool and reduces the overall size of the tool.

A further problem with electrosurgical tools having suction capability is clogging. In this regard, in electrosurgical tools having an electrode with a geometry of a plate, box, full or partial sphere, doughnut, cone or pyramid, for example, and having the electrode attached or supported by an insulating component, such tools typically have a suction opening that is fully or wholly defined by the electrode itself. When the treating portion or face of the electrode is in full or substantially complete contact with tissue, suction through the opening or openings in the electrode face can be temporarily stopped. This flow stoppage can cause charred or partially ablated tissue to become lodged or stuck on the face of the electrode and across the suction openings defined therein. Then, when the probe is removed from the tissue, the charred tissue often continues to cover the suction openings, which clogs the tool.

In an effort to minimize clogging of an electrosurgical tool as discussed above, the instant invention provides a suction opening or pathway which is defined by both the electrode and the insulator element or cap which supports the electrode on the tool. Providing a suction opening defined by the two different materials of the electrode and the insulator reduces clogging in that while charred tissue may adhere to the electrode, any charred tissue located near the insulator either does not adhere to the insulator or adheres less strongly to the insulator, so that when the suction flow resumes once the electrode is removed from contact with the tissue, any charred tissue located on the insulator is easily removed by suction. The above arrangement thus minimizes the adherence of charred tissue to the working tip of the tool, and allows easier dislodgement of any charred tissue to the working tip to maintain greater and more continuous suction flow through the tool. At least one additional suction opening can also be provided at the working tip of the tool, which opening is defined wholly by the electrode.

The above arrangement which includes at least one suction opening defined by the electrode and the non-conductive insulating element which supports the electrode can also increase the size of the suction opening at the working tip of the tool, in that the suction opening is not fully surrounded and defined by the material of the electrode itself. Providing a larger suction window or opening at the tool tip can make it more difficult to cut off the flow of suction through the tool when the electrode face is fully or largely in contact with tissue, and the more suction that is being drawn through the tool, the less chance of a clog. In this regard, when the suction flow is stopped within the tool, even if the stoppage is temporary, small pieces of tissue can deposit on nearby surfaces and cause particulate clogging within the interior of the tool.

Further, in electrosurgical tools used for mass ablation of tissue, the tool shaft and the treating surface of the electrode or electrode face are often oriented generally parallel to one another, i.e. the tool or probe is fairly sharply angled at its distal end. This configuration allows improved access to targeted areas within the surgical site, such as in a joint. However, an angled probe configuration means that the suction pathway at the distal end of the tool has two portions which are oriented transversely relative to one another, which can make clogging more frequent due to the somewhat convoluted path through which the pieces of tissue must travel after being drawn into the tool. The arrangement according to the invention is thus particularly useful in these types of tools, as same can significantly reduce the possibility of clogging of the tool.

The electrode according to the invention is also advantageous in that same incorporates reinforced areas of metal adjacent open areas of the electrode which define suction openings, which provides the electrode with improved strength and durability. Specifically, thinner areas of the electrode are provided generally centrally or inwardly on the tissue-treating surface of the electrode adjacent to suction openings formed in the treating surface of the electrode. Reinforced or thickened areas are provided on the treating surface of the electrode outwardly of these thinner areas. The thinner areas can experience wear or degradation during usage of the probe due to the passage of current therethrough. However, the reinforced areas effectively maintain the electrode intact and can provide a longer-life tool.

BRIEF DESCRIPTION OF THE DRAWINGS

FIG. 8 is an enlarged perspective side view of the insulator cap of the lumen assembly;

FIG. 9 is an enlarged plan view of the insulator cap of FIG. 8;

FIG. 10 is an enlarged longitudinal cross-sectional view of the insulator cap, as seen generally along line 10-10 in FIG. 9;

FIG. 11 is an enlarged transverse cross-sectional view of the insulator cap, as seen generally along line 11-11 in FIG. 10;

FIG. 12 is an enlarged perspective view of the insulator cap;

FIG. 13 is an enlarged perspective view of the electrode;

FIG. 14 is an enlarged cross-sectional view of the electrode foot, as seen generally along line 14-14 in FIG. 13;

FIG. 15 is an enlarged plan view of the electrode assembled to the insulator cap;

FIG. 16 is an enlarged cross-sectional view of the electrode assembled to the insulator cap, as seen generally along line 16-16 in FIG. 15;

Figure 1:
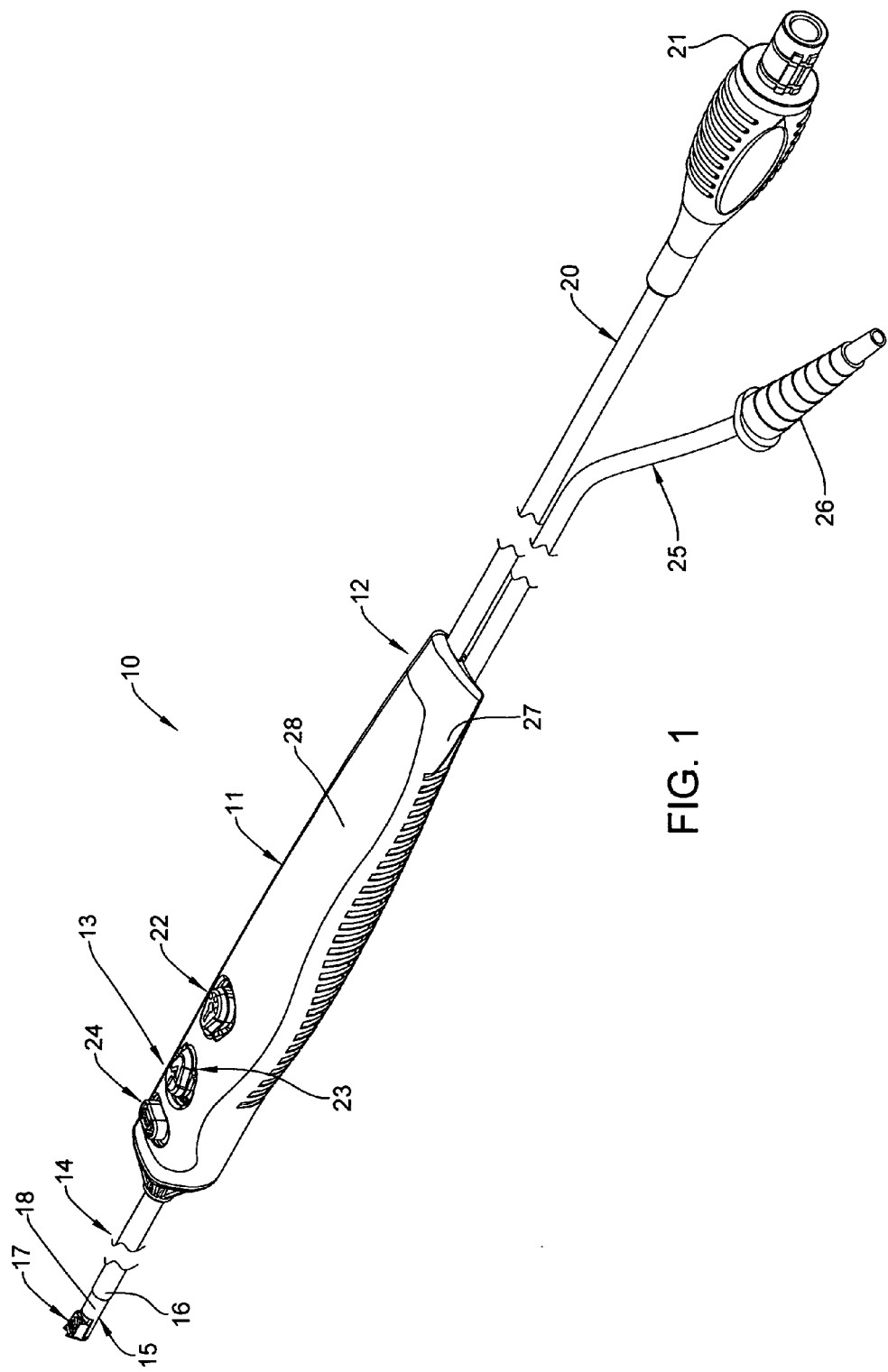
FIG. 1 is a perspective and fragmentary view of the electrosurgical tool according to the invention.

Certain terminology will be used in the following description for convenience in reference only, and will not be limiting. For example, the words "upwardly", "downwardly", "rightwardly" and "leftwardly" will refer to directions in the drawings to which reference is made. The words "inwardly" and "outwardly" will refer to directions toward and away from, respectively, the geometric center of the arrangement and designated parts thereof. The words "forwardly" and "distally" will refer to the direction toward the end of the arrangement which is closest to the patient, and the words "rearwardly" and "proximally" will refer to the direction away from the end of the arrangement which is furthest from the patient. Said terminology will include the words specifically mentioned, derivatives thereof, and words of similar import.

DETAILED DESCRIPTION

Figure 2:
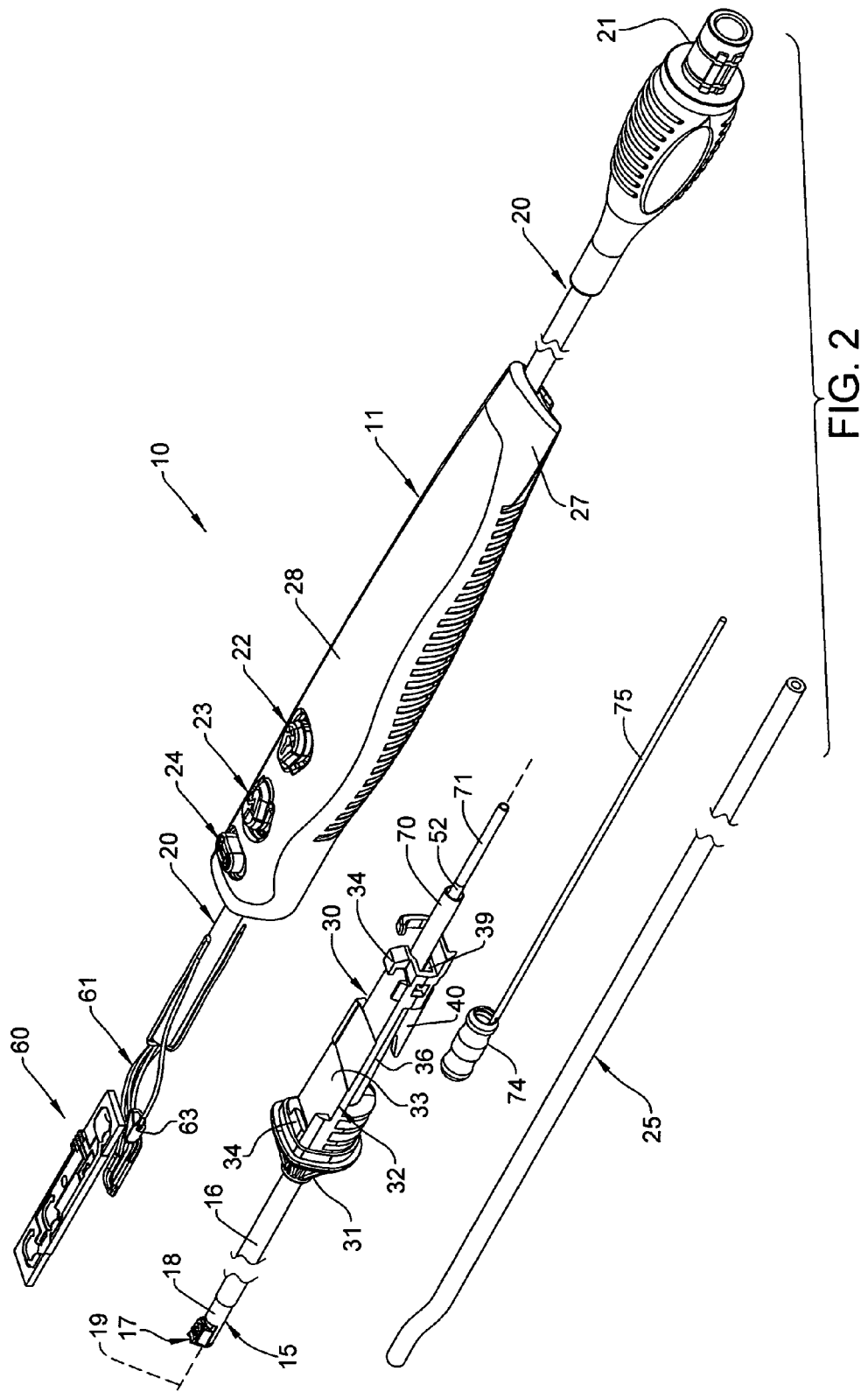
FIG. 2 is an exploded view of the tool of FIG. 1.

FIGS. 1 and 2 illustrate an electrosurgical tool 10 according to the present invention. The tool 10 includes an elongated housing 11 which serves as the handle for the tool 10. Housing or handle 11 includes a proximal end portion 12 and a distal end portion 13 spaced therefrom. A lumen assembly 14 projects forwardly or distally from the distal end portion 13 of housing 11. Lumen assembly 14 includes an outer tubular shaft 15 formed from conductive material, such as stainless steel, which outer shaft 15 is covered along a majority of the length thereof by an insulating material, such as a heat-shrink tube 16. The distal end of the lumen assembly 14 incorporates an electrode 17. In the illustrated embodiment, an exposed distal end 18 of the outer shaft 15 defines a return or reference electrode, while electrode 17 defines an active, energy-delivering electrode. For purposes of reference herein, lumen assembly 14 defines a central longitudinal axis 19.

The current for energizing tool 10 is supplied by a control console or generator (not shown), wherein current flows from the console to the tool 10 through a cable 20. Cable 20 accordingly includes a connector 21 which plugs into an appropriate port located on the console. Depending upon the surgeon's commands, the control console applies either a lower power coagulating-causing signal to electrode 17, or a high power ablation-causing signal to electrode 17. The tool 10 is controlled by three normally-open switches 22, 23 and 24 provided on housing 11. When it is desirable to operate the tool 10 in the coagulation mode, switch 22 is depressed. Switch 23 is depressed to operate the tool 10 in the ablation or cutting mode. Switch 24 is depressed to adjust the cut level. It will be appreciated that the tool 10 may alternatively be controlled with a foot switch, which typically includes a set of switches which are depressed to perform the same functions as the control console.

Housing 11 of tool 10 has a generally hollow interior through which a portion of cable 20 extends. Tool 10 is additionally provided with a suction tube 25 having a distal portion which extends into the housing 11, and a proximal portion connected to an adapter or connector 26 associated with a source of suction (not shown). Housing 10 is defined by an outer housing wall or shell 27 which may be constructed of plastic, and a cover member 28 which is fixedly attached over an opening (not shown) defined along an upper portion of housing wall 27, such as with adhesive or other type of suitable fastening arrangement. Cover member 28 in the illustrated embodiment is a membrane-like member and may be constructed of an elastomeric material. Cover member 28 has three flexible buttons which respectively define the moving components of switches 22, 23 and 24.

Figure 3:
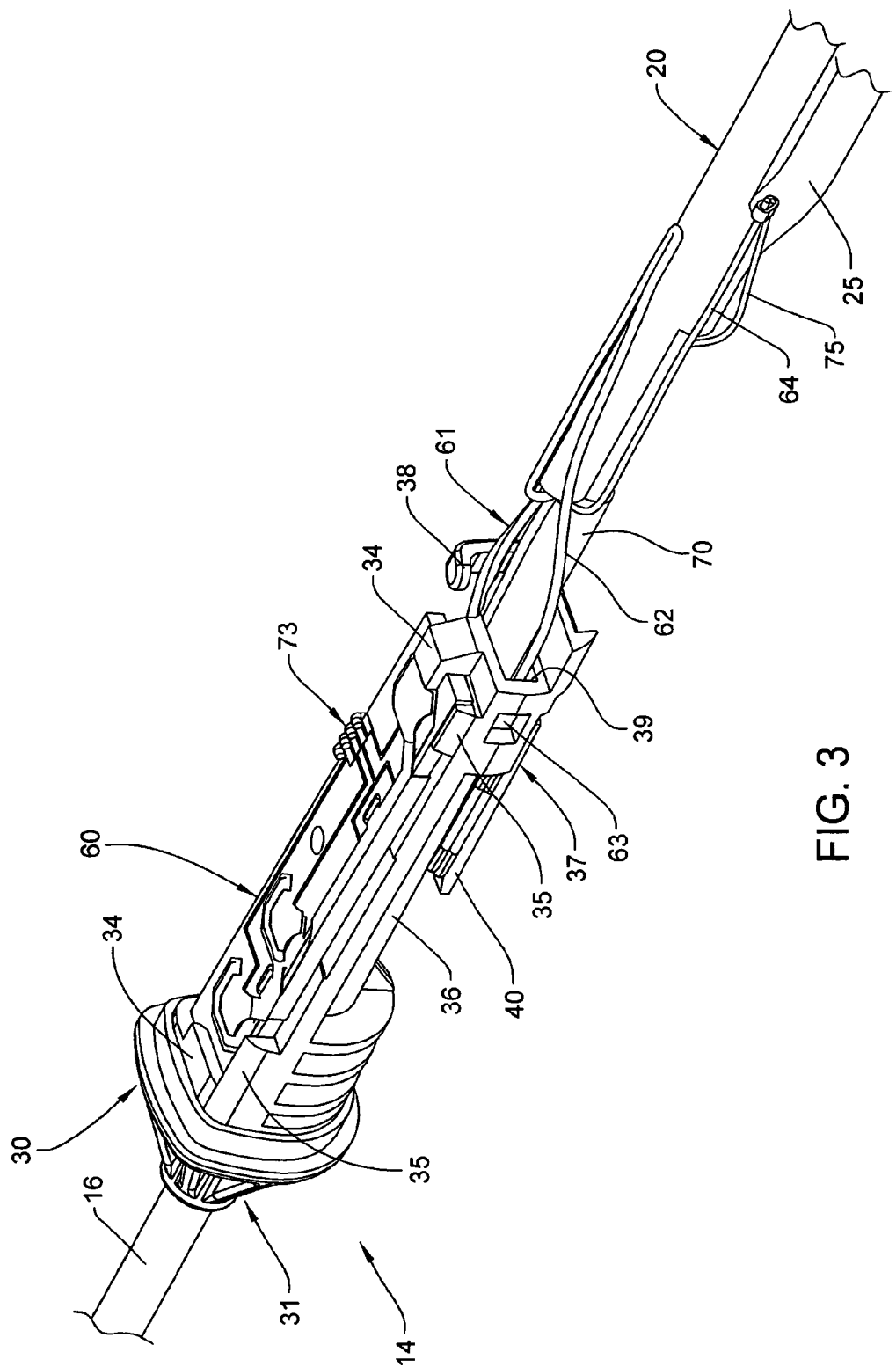
FIG. 3 is an enlarged, fragmentary view of the tool handle with the housing removed for illustrative purposes.
Figure 4:
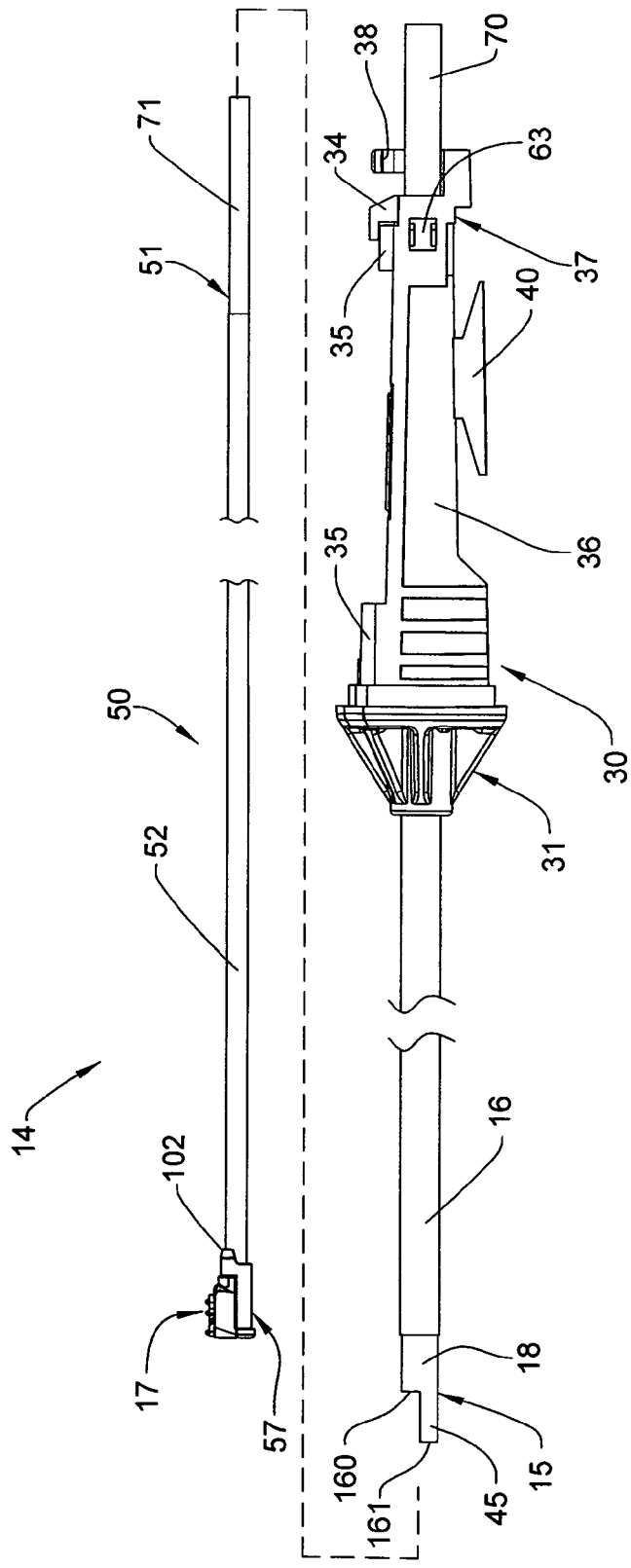
FIG. 4 is an enlarged, fragmentary exploded side view of the tool handle with the housing removed and the lumen assembly.

Turning now to lumen assembly 14, and with reference to FIGS. 2-4, assembly 14 includes a rigid base member 30 defined by a generally cone-shaped nose 31 which defines the distal end of base member 30, and a generally plate-shaped support element 32 which projects proximally from nose 31. Support element 32 defines thereon a flat support surface 33. A pair of axially-spaced retaining flanges 34 are formed on opposite ends of support surface 33 and are spaced upwardly therefrom, and a pair of guides 35 are located in a spaced-apart manner along one side of support surface 33. Base member 30 additionally includes a tubular section 36 which extends axially along the lower portion of member 30, and a wiring support section 37 which is connected to a proximal end of tubular section 36 and defines the proximal end of base member 30. Wiring support section 37 includes a generally hook-shaped guide arm 38, a wire port 39 which communicates with a hollow interior of tubular section 36, and a wire storage element 40 located at the underside of base member 30.

Base member 30 defines therein a through-bore which extends through the entire axial extent of base member 30, which through-bore opens distally through nose 31 and proximally through tubular section 36 and wiring support section 37. In the illustrated embodiment, base member 30 is formed as a one-piece, unitary member which in one embodiment may be formed from plastic via injection molding.

Figure 5:
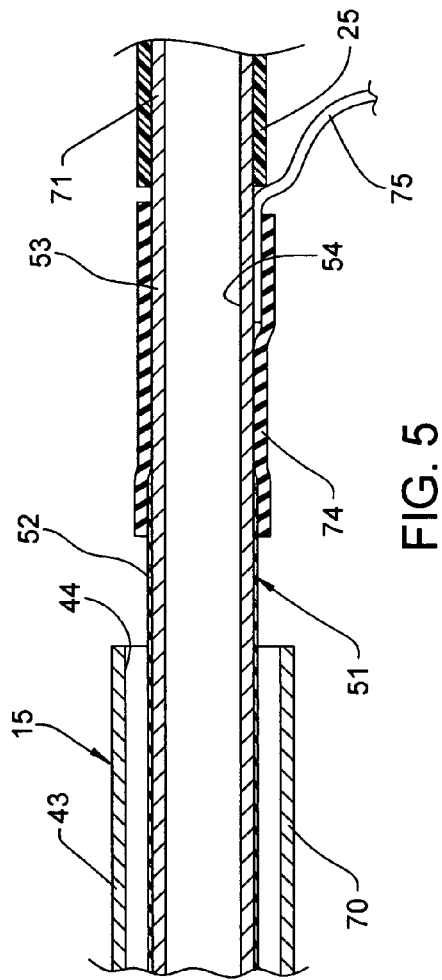
FIG. 5 is an enlarged, fragmentary longitudinal cross-sectional view of the proximal end of the lumen assembly.
Figure 6:
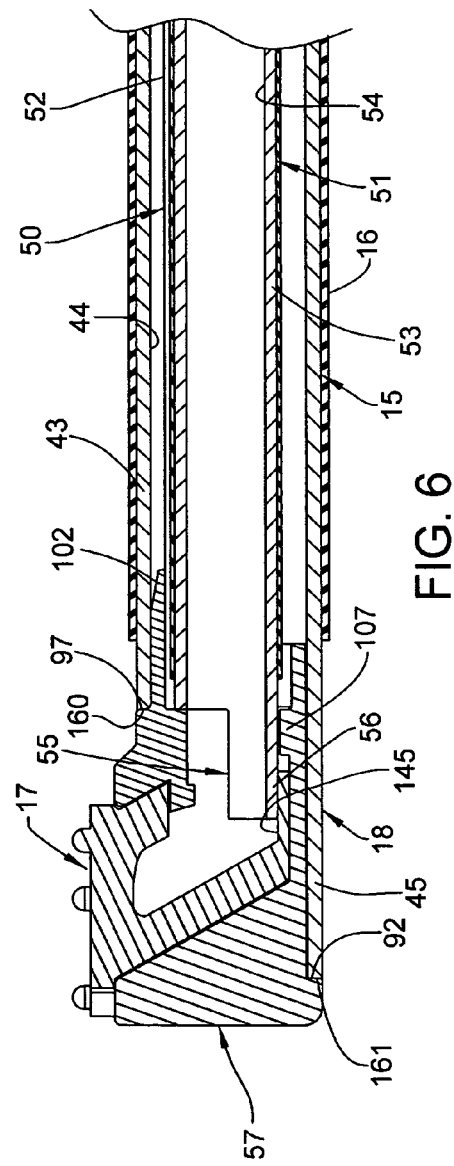
FIG. 6 is an enlarged, fragmentary longitudinal cross-sectional view of the distal end of the lumen assembly.
Figure 7:
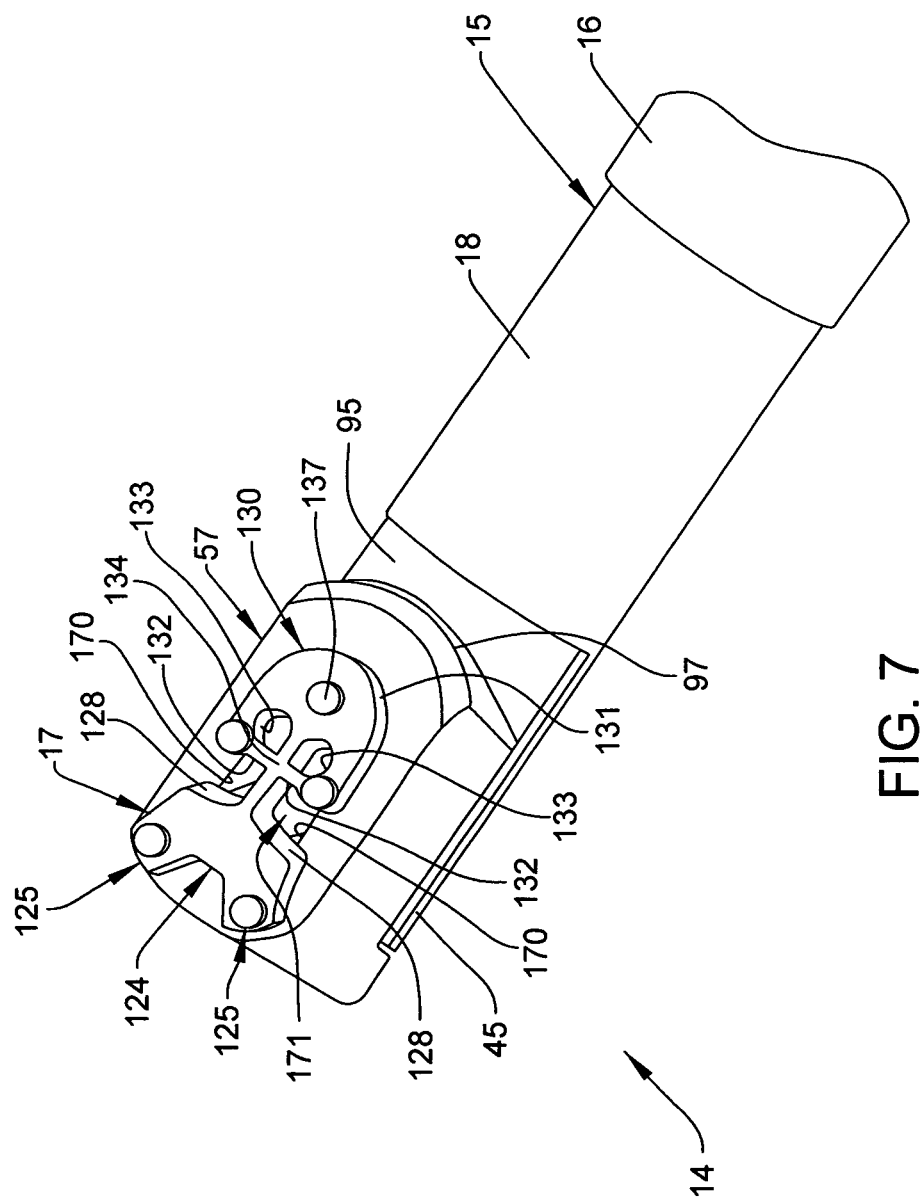
FIG. 7 is an enlarged, fragmentary perspective plan view of the distal end of the lumen assembly.

As shown in FIGS. 4-6, outer shaft 15 of lumen assembly 14 is defined by a tubular wall 43 which defines a hollow interior conduit 44 extending along the entire axial extent of shaft 15. The distal end 18 of shaft 15 projects beyond the terminal distal end of insulator tube 16 disposed on the outer surface of shaft 15. In the illustrated embodiment, the distal end 18 of shaft 15 is formed by removing approximately the upper half of tubular wall 43 of outer shaft 15, which provides distal end 18 with a flange 45 having an arcuate, trough-like shape which opens upwardly and defines the terminal distal end of shaft 15.

Lumen assembly 14 further includes an inner shaft assembly 50 disposed within outer shaft 15. Inner shaft assembly 50 includes a tubular inner shaft 51 formed from conductive material, such as stainless steel, and covered along a majority of the length thereof by an insulating material, such as a heat-shrink tube 52. Inner shaft 51 is defined by a tubular wall 53, which tubular wall 53 defines an interior conduit 54 extending along the length of shaft 51. Inner shaft 51 has a distal end 55 configured similarly to distal end 18 of outer shaft 15. Specifically, distal end 55 of inner shaft 51 is formed by removing approximately the upper half of tubular wall 53, which results in a flange 56 having an arcuate and trough-like shape which opens upwardly. Distal end 55 of inner shaft 51 is mounted within an insulator cap 57, which insulator cap or electrode support or electrode support element 57 supports electrode 17 and insulates same from the distal end 18 of outer shaft 15 as discussed further below.

Tool 10 additionally includes a circuit board 60, as shown in FIGS. 2 and 3. In this regard, cable 20 includes a wiring bundle 61 which exits a distal end of cable 20 and is connected to board 60. A wire 62 carried by cable 20 has a terminal end removably mounted within wire port 39 of base 30 via a spring clip 63. Cable 20 additionally carries wire 64, which wire 64 is associated with inner shaft 51 as discussed further below.

Outer shaft 15 is mounted within the bore defined in base 30, and extends distally from nose 31 thereof. It will be appreciated that the portion of shaft 15 which projects distally from nose 31, except for exposed distal end 18, is covered with insulator tube 16. As shown in FIG. 2, outer shaft 15 extends through tubular section 36 and has a proximal end portion 70 which is not covered by insulator tube 16 and which extends proximally from tubular section 36 of base member 30. Inner shaft 51 likewise has a proximal end portion 71 which is uncovered by insulator tube 52.

Circuit board 60 is assembled to base 30 by placing board 60 atop support surface 33 so that the opposite axial ends of board 60 are retained by flanges 34 and so that one longitudinal side edge thereof is engaged with guides 35. Adhesive may also be used to secure circuit board 60 to base 30. Wire bundle 61 from cable 20 extends under guide 38, around storage element 40 and is then connected to circuit board 60 at a connection area 73. Return wire 62 of cable 20 is electrically connected to the exposed proximal end portion 70 of outer shaft 15 by means of spring clip 63, which clip 63 electrically contacts the outer surface of shaft 15 within wiring support section 37.

With reference to FIGS. 8-11, insulator cap 57 of lumen assembly 14 is of a generally tubular construction, and includes a distal portion 80 which is configured to support and insulate electrode 17, and a proximal portion 81 configured to receive distal end 55 of inner shaft 51. Cap 57 is constructed of insulating material, such as ceramic. Distal portion 80 is defined by an outer wall which is generally annular in shape. This outer wall includes a distal wall 82 which is generally wedge-shaped when viewed in cross-section, a pair of laterally-spaced side walls 83 oriented transversely to distal wall 82, and a proximal wall 84 axially spaced from distal wall 82 and interconnecting the respective side walls 83. Walls 82, 83 and 84 have respective inner surfaces which define an electrode-receiving bore 85 within distal portion 80. In this regard, an inner surface 86 of distal wall 82 and an inner surface 87 of proximal wall 84 are angled and generally parallel to one another such that bore 85 projects or angles proximally as same extends downwardly into cap 57. Bore 85 opens upwardly through a generally annular and planar upper surface 88 of distal portion 80.

Proximal portion 81 is joined to distal portion 80 at lower ends of the walls 82, 83 and 84 thereof. Portion 81 is defined by a generally cylindrical wall 90 having a longitudinal axis which coincides with axis 19 of tool 10. As shown in FIG. 10, distal wall 82 of distal portion 80 projects downwardly beyond an outer surface 91 of wall 90 so as to define a semi-circular, proximally-facing and generally upright step surface 92 which extends, in the illustrated embodiment, approximately 180° around the lower portion of cylindrical wall 90. Proximal wall 84 of distal portion 80 defines an angled outer surface 93, and proximal portion 81 has a semi-circular wall portion 95 joined to outer surface 93 and extending proximally therefrom. Wall portion 95 extends approximately 180° around the upper portion of cylindrical wall 90 and is joined thereto at a semi-circular, proximally-facing and generally upright step surface 97 which defines the proximal terminal edge of wall portion 95. With reference to FIG. 10, proximal wall 84 of distal portion 80 includes a generally horizontal support wall 100 located within cap 57 and having an upwardly-facing surface 101 which is joined to surface 87 and is oriented transversely relative thereto.

Cylindrical wall 90 at its proximal end is joined to an arcuate flange 102 which projects axially beyond a lower semi-circular terminal edge of wall 90. Flange 102, at its proximal end, has an outer and generally upwardly-facing surface 103 which extends at a slight downward angle relative to the horizontal as same projects proximally. Proximal wall 84 of distal portion 80 and cylindrical wall 90 together define a bore 105 which communicates with bore 85 and opens proximally through terminal proximal edge of wall 90 and arcuate flange 102. Bore 105 has a proximal inner diameter D1 and a distal inner diameter D2, wherein distal diameter D2 is of a lesser diameter than diameter D1. A step 107 is defined by cylindrical wall 90 approximately midway along the longitudinal extent of bore 105. Wall 90 additionally defines an upwardly arcuate inner surface 108 which terminates proximally at a generally upright step surface 109 which faces inner surface 86 of inner wall 82 of distal portion 80. Inner surface 108 terminates distally at an arcuate junction 110 with inner surface 86 of wall 82.

Turning now to electrode 17, and with reference to FIGS. 7 and 13-16, same includes an upper and generally plate-like tissue-treating element 120 and a mounting structure 121 defined by a distal leg 122 and a proximal leg 123, which legs project downwardly from element 120. Electrode 17 in the illustrated embodiment is constructed of conductive metal, such as a tungsten alloy, and in one embodiment may be formed by metal injection molding. Upper tissue-treating element 120 has a plate-like and generally U-shaped distal section 124 defined by a pair of legs 125 which angle outwardly and away from one another as same project in the distal direction, and an intermediate section 126 interconnecting legs 125. Further, each leg 125 has a generally upwardly-projecting tissue-treating protrusion 127 defined at an outer terminal end thereof. Each leg 125 has a proximally-facing and generally upright outer surface 128. Element 120 additionally includes a plate-like proximal section 130 having the shape of a partial ellipse defined by a rounded proximal edge surface 131 and a pair of generally straight distal edge surfaces 132 which are interrupted by a bridge 129 which interconnects distal section 124 and proximal section 130. A pair of openings 133, which in the illustrated embodiment are tear drop-shaped, extend completely through section 130 adjacent edge surfaces 132 and are separated from edge surfaces 132 by a narrow strip 134 of section 130, which strip 134 is oriented transversely to bridge 129. A pair of upwardly-projecting tissue-treating protrusions 136 are disposed at respective distal corners of section 130 at opposite ends of strip 134, and a further tissue-treating protrusion 137 is located proximally of openings 133.

Distal section 124 and proximal section 130 are connected to one another by a narrow strip of material or bridge 129, which adjoins strip 134. Bridge 129 has a pair of outer and oppositely-facing edge surfaces 138 which are generally upright and join to the respective outer edge surfaces 128 of the legs 125, and to the respective edge surfaces 132 of strip 134.

With respect to mounting structure 121, distal leg 122 has a first leg part 142 connected to a lower side of U-shaped distal section 124. First leg part 142 extends proximally as same projects away from section 124 and downwardly such that first leg part 142 is oriented at an angle relative to the horizontal. Distal leg 122 has a second leg part or foot 144 which projects proximally from a lower end of first leg part 142 and is generally horizontally oriented. Second leg part 144 has oppositely-facing upper and lower arcuate surfaces 145 and 146, which are generally parallel to one another as shown in FIG. 14. First leg part 142 has a distally-facing surface 148 which is outwardly arcuate or convex, and a lower edge of surface 148 joins to lower surface 146 of second leg part 144.

Proximal leg 123 is connected to and projects downwardly from a lower side of proximal section 130. Leg 123, similar to first leg part 142, extends proximally as same projects away from section 130 and downwardly such that leg 123 is oriented at an angle relative to the horizontal, and is generally parallel to, but spaced proximally from, first leg part 142. As best shown in FIG. 16, leg 123 has a lesser length than first leg part 142, and in the illustrated embodiment is about one-fourth the length of leg part 142. Leg 123 has a proximally-facing outer surface 150 which is outwardly arcuate or convex.

Electrode 17 is assembled to insulator 57 by applying adhesive to distal surface 148 of distal leg 122 and to proximal surface 150 of proximal leg 123. Electrode 17 is then positioned above upper surface 88 of distal portion 80 of insulator 57, and legs 122 and 123 are inserted into bore 85 of insulator 57 so that distal leg 122 is positioned adjacent inner surface 86 of distal wall 82 and so that proximal leg 123 is positioned adjacent inner surface 87 of proximal wall 84. Electrode 17 is then pushed downwardly into insulator 57 so as to effectively position tissue-treating element 120 of electrode 17 atop upper annular surface 88 of insulator 57. The distal surface 148 of leg 122 and proximal surface 150 of leg 123 each have an outwardly-arcuate or convex shape so as to correspond to the inwardly-arcuate shapes of the respective surfaces 86 and 87 of insulator cap 57, so as to securely position electrode 17 within insulator cap 57. Further, the lower terminal end of leg 123 is supported atop wall 100 of cap 57.

Inner shaft 51 and insulator 52 are assembled to electrode 17 and insulator cap 57 by applying adhesive to appropriate surfaces of distal end 55 of shaft 51 and inserting distal end 55 in a distal direction into proximally-opening bore 105 of insulator 57. Shaft 51 is advanced distally so that arcuate flange 56 of shaft 51 slides over upper arcuate surface 145 of leg part or foot 144 of electrode 17 so as to make electrical contact therewith. In this regard, the upwardly arcuate or convex curvature of electrode foot 144 corresponds to the curvature of the outer surface of flange 56 of shaft 51 so as to provide adequate surface area contact between these components. Further, the flange 56 of shaft 51 exerts a slight downward pressure on foot 144 of electrode 17 to ensure adequate electrical contact therewith and also to help secure electrode 17 within insulator cap 57. Distal advancement of shaft 51 is continued until the terminal upper distal edge of shaft 51 abuts a shoulder 200 (FIG. 16) of insulator cap 57, which shoulder 200 defines the terminal distal end of bore 105. The step 107 of insulator cap 57 can serve as a guide for shaft 51 during insertion into bore 105 to help position flange 56 atop electrode foot 144. Further, the portion of bore 105 of cap 57 having diameter D1 is large enough to accommodate shaft 51 and insulator 52, and also serves as a space for receiving adhesive applied to distal end 55 of shaft 51.

Inner shaft 51, assembled to electrode 17 and insulator cap 57 as discussed above, is assembled to outer shaft 15 and base member 30 by inserting the proximal end 71 of inner shaft 51 into the open distal end 18 of outer shaft 15. Inner shaft 51 is advanced proximally through outer shaft 15 until an upper terminal distal edge 160 of outer shaft 15 slides over flange 102 of insulator cap 57 and abuts and seats against step surface 97 of insulator cap 57. At the same time, lower arcuate flange 45 of outer shaft 15 slides over the lower side of wall 90 of insulator cap 57 until a terminal distal edge 161 of flange 45 abuts and seats against step surface 92 of distal wall 82 of insulator cap 57. Adhesive may be applied to appropriate outer surfaces of insulator cap 57 so as to fixedly secure insulator 57 to the distal end 18 of outer shaft 15. With inner shaft 51 so assembled to base member 30, the proximal end portion 71 of shaft 51 extends beyond the proximal end portion 70 of shaft 15, as shown in FIG. 2. As shown in FIGS. 2 and 5, a heat shrink or solder band 74 is provided around proximal end portion 71 of inner shaft 51 and secures a wire 75 in electrical contact with shaft 51. Wire 75 is then crimped or connected to wire 64 of cable 20.

As shown in FIG. 5, the proximal end portion 71 of inner shaft 51 which projects proximally beyond solder band 74 is inserted into a terminal distal end of suction tube 25 so that suction can be drawn through conduit 54 of inner shaft 51.

The lumen assembly 14 connected to cable 20 and suction tube 25 is enclosed within housing shell 27, and cover member 28 is adhesively or otherwise secured to housing shell 27 so as to seal off the interior thereof. When cover member 28 is secured to housing shell 27, switches 22, 23 and 24 are positioned over respective contact pads defined on circuit board 60, and when switch 22, 23 or 24 is depressed, the circuit is completed and actuation of the tool 10 occurs as desired. Cable 20 and suction tube 25 extend outwardly through respective bores defined in the proximal end of housing 11 for connection to the console and suction source, respectively.

It will be appreciated that the above-discussed assembly steps are provided only as an example, and other assembly methods are contemplated by the invention.

With the various components assembled as discussed above, insulator cap 57 fully insulates active electrode 17 from return electrode or distal 18 of shaft 15. Further, with reference to FIG. 7, the electrode 17, insulator cap 57 and inner shaft 51 together define a suction conduit through tool 10 which provides suction at the surgical site. In this regard, a plurality of suction openings are defined at the distal end of lumen assembly 14. Specifically, the pair of openings 133 defined by proximal section 130 of electrode 17 open into bore 85 of cap 57, and thus are in communication with bore 105 of insulator cap 57, bore 54 of inner shaft 51 and suction tube 25. An additional pair of openings are defined by the respective surfaces 132, 138 and 128 of electrode 17 and inwardly-facing and generally upright edge surfaces 170 of side walls 83 of insulator cap 57, which edge surfaces 170 extend longitudinally between the respective adjacent surfaces 128 and 132 and are disposed in opposed and spaced relation with the respective surfaces 138 of bridge 129. These suction openings 171 are disposed distally from openings 133. Suction can therefore be drawn into tool 10 via suction openings 133 and 171.

Suction openings 133, in the illustrated embodiment, are fully or wholly defined by the tissue-treating element 120 of electrode 17, while suction openings 171 are defined only partially by element 120. Specifically, suction openings 171 are defined in part by surfaces 132, 138 and 128 of element 120 of electrode 17 and in part by edges 170 of side walls 83 of insulator cap 57. Therefore, there is always at least one suction pathway defined by the combined geometry of both the electrode 17 and the insulator cap 57. With suction openings 171 which are not wholly defined by tissue-treating element 120 of electrode 17, when the tissue treating element 120 is in full contact with tissue and the tissue is ablated, suction flow can stop temporarily and charred tissue may stick to the electrode 17. However, any charred tissue near the insulator cap 57 does not stick to, or is adhered with less force to, the insulator cap 57, due to the properties of the ceramic material thereof. When the tool 10 is removed from the tissue and suction resumes, any charred tissue is easily removed from the insulator cap 57 by the suction of the tool since such tissue does not adhere strongly to the insulator 57.

Further, the conductive inner shaft 51 serves as a suction conduit through the tool 10. In this regard, the inner shaft 51, by being constructed of a conductive material and electrically connected to cable 22 as discussed above, additionally serves as a means for providing electrical current to the electrode 17 via the electrical contact between electrode 17 and distal end 55 of inner shaft 51. This configuration provides the ability to reduce the overall size of the tool, by effectively eliminating the need for electrical wiring to extend through the length of the lumen assembly 14, and also by integrating the functions of energy delivery and suction into one component, i.e. the inner shaft 51.

In electrosurgical tools used for mass ablation of tissue, the longitudinal axis of the tool shaft and the plane in which the treating surface of the electrode (or the suction openings defined at the treating surface of the electrode) is located can be oriented generally parallel to one another. This means that the suction pathway which extends from the suction openings at the electrode treating surface and through the distal end of the tool towards the suction source has portions which can be transversely oriented relative to one another at a fairly large angle, for example at a 90° orientation. This is illustrated in FIG. 16 which shows bores 85 and 105. The suction pathway at the distal end of the tool 10 thus has two portions defined by bores 85 and 105 which are oriented transversely relative to one another, which can make clogging more frequent due to the relatively severely angled orientation of the conduit or path through which the tissue fragments must travel after being drawn into the tool 10. The arrangement according to the invention is thus particularly useful in these types of tools, as same can significantly reduce the clogging of the tool.

The electrode 17 according to the invention is also advantageous in that same has a configuration which provides reinforced areas adjacent open areas of the electrode 17, such as suction openings 133 and 171, which provides the electrode 17 with increased strength and thus may allow the probe 10 to be used for a greater length of time during a surgical procedure.

Figure 17:
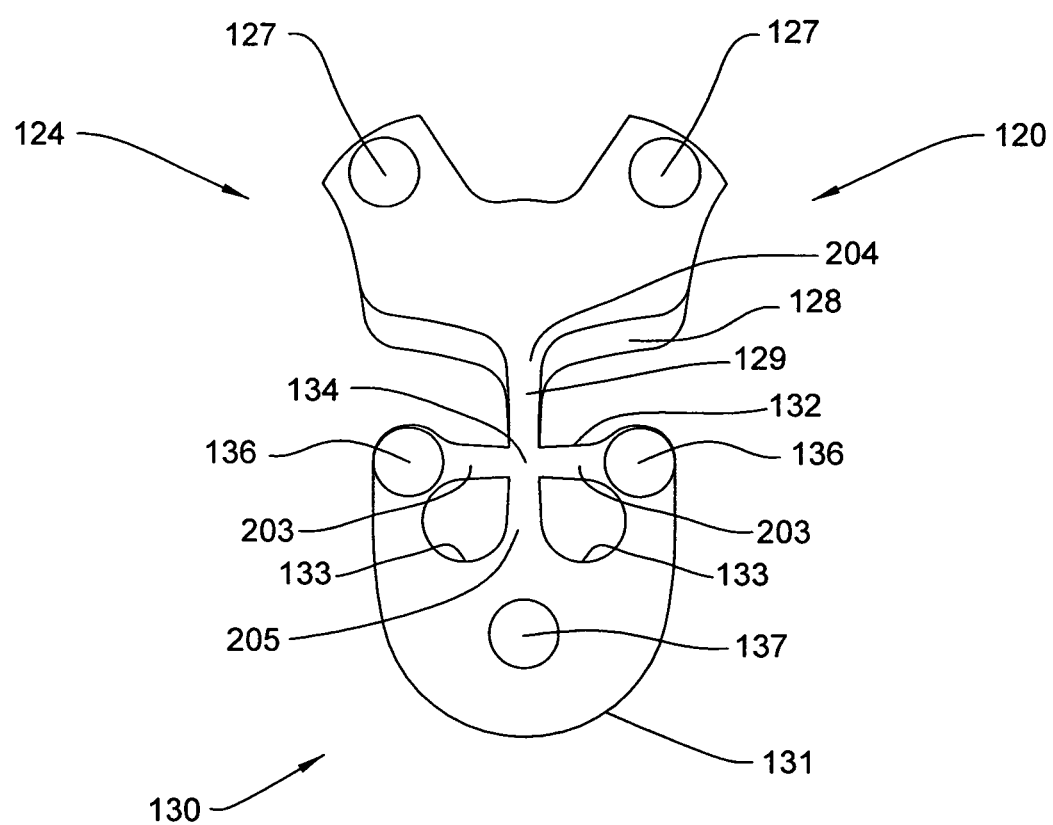
FIG. 17 is an enlarged plan view of the tissue-treating element of the electrode in isolation.

Specifically, and with reference to FIG. 17, the strip 134 which borders or defines the distal side of the openings 133 gradually widens or thickens (as measured in the direction of the drawing plane of FIG. 17) as same projects sidewardly in opposite directions away from bridge 129 and towards the respective tissue-treating protrusions 136. This widening of strip 134 effectively defines respective reinforced areas 203 which are located closely adjacent the respective protrusions 136 and outwardly from the intersection of bridge 129 and strip 134. In a similar manner, bridge 129 widens as same projects in opposite directions away from strip 134 and towards distal tissue-treating protrusions 127 and proximal tissue-treating protrusion 137, so as to define respective distal and proximal reinforced or thickened areas 204 and 205.

With the above configuration, the thinner areas of the electrode 17, such as the innermost or central areas of the bridge 129 and strip 134, are clustered together near the center of the electrode 17. Should these innermost areas undergo wear or degrade during a procedure due to the passage of current therethrough, the surrounding areas of the electrode 17 i.e. reinforced areas 203, 204 and 205, will maintain the electrode 17 intact and allow the tool to be used for a longer period of time. The above design avoids having to provide the electrode with a thicker dimension (as measured generally perpendicular to the drawing plane of FIG. 17) to increase the durability thereof. In this regard, providing an electrode with a thicker dimension (in the direction perpendicular to the drawing plane of FIG. 17) can lead to increased probe clogging since such a configuration requires that the particulate suctioned away from the surgical site travel a further distance, which can make it more likely that particles will become stuck and eventually lead to a clog in the probe.

Figure 18:
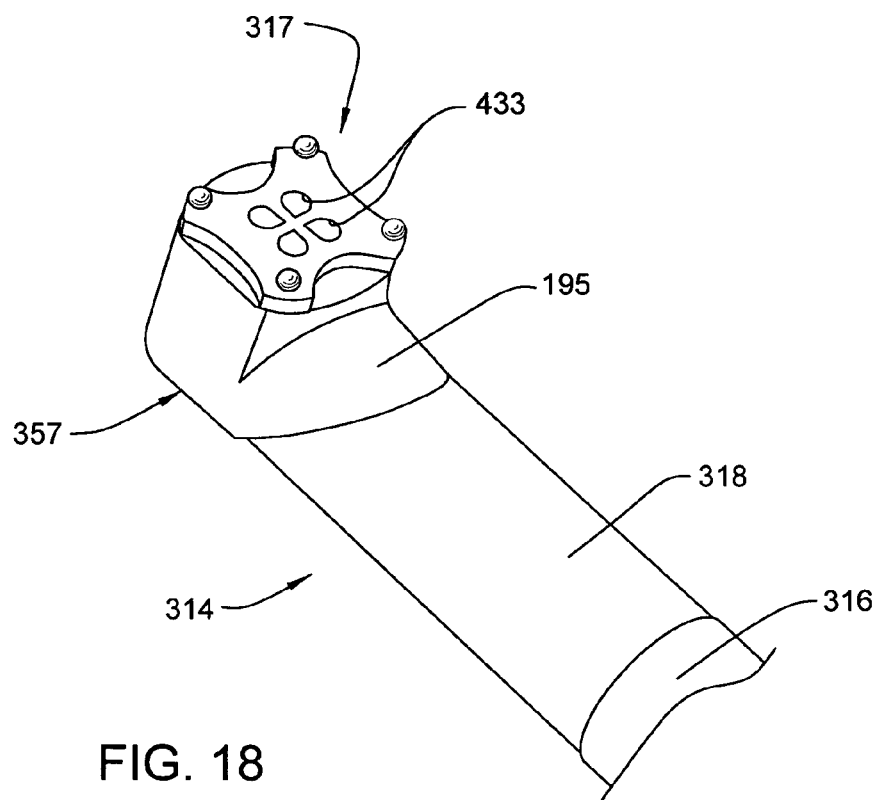
FIG. 18 is an enlarged, fragmentary perspective plan view of the distal end of an alternative embodiment of the lumen assembly.
Figure 19:
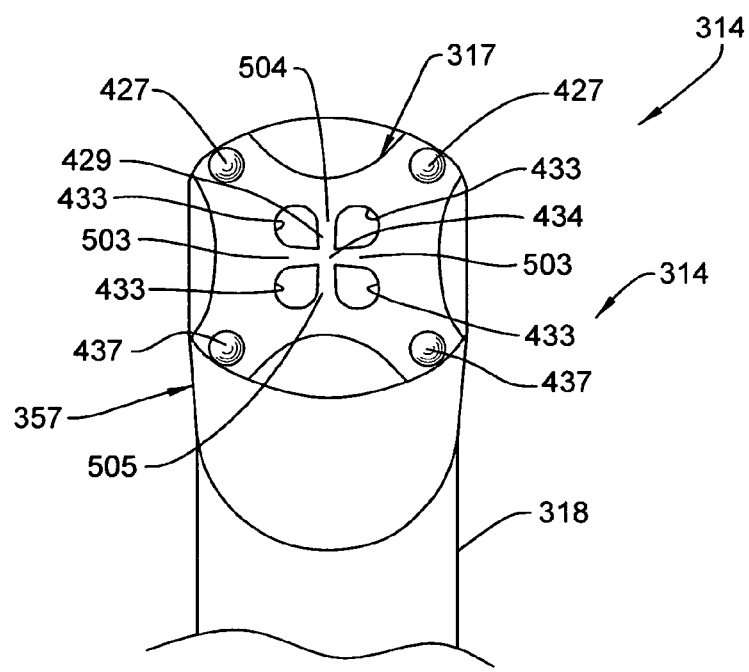
FIG. 19 is an enlarged and fragmentary plan view of the embodiment of the lumen assembly of FIG. 18.

FIGS. 18 and 19 illustrate an alternative embodiment of a lumen assembly 314 according to the invention. Components of lumen assembly 314 which are identical or similar to components of lumen assembly 14 discussed above are identified with the same reference number, plus three-hundred. The lumen assembly 314 of FIGS. 17 and 18 primarily differs from the lumen assembly 14 in that the electrode 317 fully or wholly defines the suction openings 433, and thus no suction openings are defined by both the electrode 317 and insulator cap 357.

In this embodiment, as in the prior embodiment, the electrode 317 has thickened or reinforced areas 503 at the opposite ends of strip 434, which strip 434 is located between the respective distal and proximal pairs of openings 433, and reinforced areas 504 and 505 located at the opposite ends of bridge 429, which bridge 429 is located between the respective right and left side pairs of openings 433 transversely to strip 434.

The electrode configuration shown in FIGS. 18 and 19, as in the prior embodiment, locates the thinner areas of the electrode 317 near the center of same. Accordingly, should the electrode 317 degrade or wear during use, such wear may occur at the thinner electrode areas, and the reinforced areas 503, 504 and 505 will maintain the electrode 317 intact.

Although particular preferred embodiments of the invention have been disclosed in detail for illustrative purposes, it will be recognized that variations or modifications of the disclosed apparatus, including the rearrangement of parts, lie within the scope of the present invention.

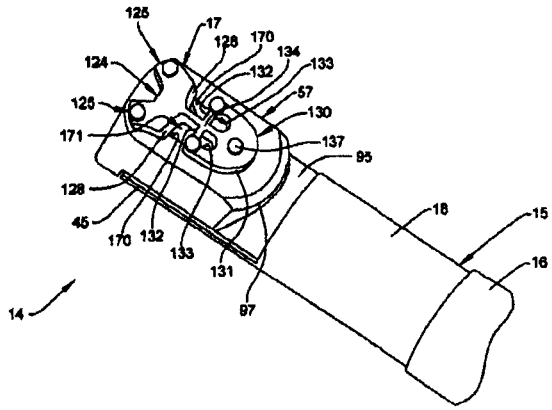

What is claimed is:

1. An electrosurgical tool comprising a handle defining a proximal end portion of said tool, an elongate tubular shaft projecting from said handle and defining a hollow interior in communication with a suction source, an electrode support element disposed at a distal end of said shaft and having a portion comprising an insulating material, said support element mounting thereon an electrode configured for electrically treating tissue at the distal end of said shaft, said electrode and said portion of said support element together defining a first suction opening in communication with said hollow interior of said shaft, said first suction opening being defined by an edge of said electrode and an edge of said portion of said support element disposed adjacent said edge of said electrode, said electrode defining a second suction opening in communication with said hollow interior of said shaft, said second suction opening being wholly defined by said electrode, and said first and second suction openings permitting suction to be drawn into and through said first and second suction openings and along said shaft to the suction source.

2. The tool of claim 1, wherein said shaft is an inner shaft, and said tool further comprises an outer tubular shaft defining a hollow interior in which said inner shaft is disposed, said outer shaft having a distal end comprising an electrically conductive material and defining a return electrode.

3. The tool of claim 2, wherein said support element is mounted within an open distal end of said outer shaft, and said distal end of said inner shaft is mounted within an open proximal end of said support element.

4. The tool of claim 3, wherein said inner shaft is constructed of electrically conductive material, and said distal end of said inner shaft is disposed in electrical contact with a portion of said electrode such that said inner shaft delivers electrical energy to said electrode.

5. The tool of claim 1, wherein said support element defines an electrode receiving opening therein in which said electrode is mounted, an outer edge area of said support element partially defining said electrode receiving opening, and said outer edge area of said support element includes said edge of said portion.

6. The tool of claim 5, wherein said second suction opening is wholly defined and enclosed by a portion of said electrode disposed adjacent said first suction opening.

7. An electrosurgical tool comprising: a handle defining a proximal end portion of said tool; a lumen assembly projecting from a distal end portion of said handle and including an elongated outer shaft defining a hollow interior, a distal end of said outer shaft comprising an electrically conductive material and defining a return electrode, an elongated inner shaft disposed within said interior of said outer shaft and defining a hollow interior in communication with a source of suction, an electrode support mounted at said distal end of said outer shaft, an active, energy-delivering electrode mounted on said electrode support, said electrode support having a portion comprising insulating material, said portion and said electrode together defining a first opening which opens outwardly adjacent an exterior portion of said lumen assembly, the first opening being in communication with said hollow interior of said inner shaft to provide suction at a distal end of said tool, said inner shaft comprising a conductive material and being connected to a source of electrical energy and disposed in electrical contact with said electrode such that said inner shaft delivers electrical energy to said electrode; said first opening being defined by an edge of said electrode and an edge of said portion of said support comprising insulating material, said electrode defining a second opening in communication with said hollow interior of said inner shaft, said second opening being wholly defined by said electrode.

8. The tool of claim 7, wherein said distal end of said outer shaft is hollow and said electrode support is mounted in said distal end of said outer shaft, said inner shaft having a distal end disposed within an open proximal end of said electrode support.

9. The tool of claim 8, wherein said distal end of said inner shaft is disposed in electrical contact with part of said electrode.

10. The tool of claim 7, wherein said electrode support defines therein a bore which opens outwardly through an annular edge portion of said electrode support, said electrode being disposed within said bore and having a leg which extends through said bore and is disposed in electrical contact with a distal end of said inner shaft.

11. The tool of claim 10, wherein said outer shaft defines a central longitudinal axis, said bore having a first bore portion which opens outwardly through said annular edge portion of said electrode support, and a second bore portion which extends in a direction substantially parallel to the longitudinal axis and transversely to said first bore portion, said leg of said electrode and said distal end of said inner shaft both being disposed within said second bore portion of said electrode support.

12. An electrosurgical tool comprising a handle defining a proximal end portion of said tool, an elongate tubular shaft projecting from said handle and defining a hollow interior in communication with a suction source, said shaft defining a central longitudinal axis, an electrode support element disposed at a distal end of said shaft and having a portion comprising an insulating material, said support element mounting an electrode thereon, said electrode having a tissue treating surface oriented in a plane which is generally parallel to the longitudinal axis of said shaft, said electrode and said portion of said support element together defining a peripheral boundary of an exterior opening in communication with said hollow interior of said shaft to permit suction to be drawn through and along said shaft through said opening to the suction source, said exterior opening defining an outermost portion of said hollow interior; wherein said exterior opening is a first opening, and said electrode defines a second opening adjacent said first opening and in communication with said hollow interior of said shaft to permit suction to be drawn through and along said shaft through said second opening to a suction source, said second opening being defined solely by said electrode.

13. The tool of claim 12, wherein said support element defines a bore therein in which said electrode is disposed, said bore having a first bore portion which opens in said plane of said electrode treating surface, and a second bore portion which extends in a direction generally parallel to the longitudinal axis and transversely to said first bore portion, said support element having an annular edge portion which defines an opening of said first bore portion in said plane of said electrode treating surface, said portion of said support element comprising said insulating material forming part of said annular edge portion.

14. The tool of claim 12, wherein said shaft is an inner shaft and said tool further comprises an outer shaft having a hollow interior in which said inner shaft is disposed, said outer shaft having a distal end comprising an electrically conductive material and defining a return electrode.

15. The tool of claim 14, wherein said support element is mounted within an open distal end of said outer shaft, and the distal end of said inner shaft is mounted within an open proximal end of said support element.

16. The tool of claim 15, wherein said inner shaft is constructed of electrically conductive material, and said distal end of said inner shaft is disposed in electrical contact with a portion of said electrode such that said inner shaft delivers electrical energy to said electrode.

17. The tool of claim 16, wherein said support element defines therein a bore which opens outwardly through an outer annular edge portion of said support element, said electrode being disposed within said bore, said portion of said electrode extending through said bore and being disposed in electrical contact with said distal end of said inner shaft, said bore having a first bore portion which opens outwardly through said outer annular edge portion of said support element, and a second bore portion which extends in a direction substantially parallel to the longitudinal axis and transversely to said first bore portion, said portion of said electrode and said distal end of said inner shaft both being disposed within said second bore portion of said support element.

18. The tool of claim 6, wherein said outer edge area of said support element is a first outer edge portion and said edge of said electrode is a first edge, said electrode and said outer edge area of said support element together define an additional first suction opening in communication with said hollow interior of said shaft, said additional first suction opening being defined by a second outer edge area of said support element which partially defines said electrode receiving opening and a second edge said electrode disposed adjacent said second outer edge area, said electrode defines an additional second suction opening wholly defined and enclosed by an additional portion of said electrode, said first suction opening and said additional first suction opening being disposed adjacent said second suction opening and said additional second suction opening.

19. The tool of claim 7, wherein said opening is defined by an edge of said portion of said electrode support and an edge of said electrode disposed adjacent said edge of said portion.

20. An electrosurgical tool comprising a handle defining a proximal end portion of said tool, an elongate tubular shaft projecting from said handle and defining a hollow interior in communication with a suction source, said shaft defining a central longitudinal axis, an electrode support element disposed at a distal end of said shaft and comprising an insulating material, said support element having an open distal end which opens outwardly and communicates with said hollow interior of said shaft, an electrode mounted within said open distal end of said support element for electrically treating tissue, said electrode having a tissue treating member oriented in a plane which is generally parallel to the longitudinal axis of said shaft and which is disposed over said open distal end of said support element, said tissue treating member including first and second elongated strips disposed in intersecting relation with one another at an intersecting area, said tool including a plurality of first and second suction openings each disposed outwardly from said intersecting area, said first and second suction openings being disposed in fluid communication with said hollow interior of said shaft to permit suction to be drawn from a surgical site inwardly through said suction openings and along said shaft to the suction source associated with said tool, each said first and second suction opening having an inner edge defined by a terminal edge of one of said first and second strips, and one of said first and second strips having an inner width dimension located adjacent said intersecting area and a pair of outer width dimensions spaced from said inner width dimension and located on opposite sides of said intersecting area, and said outer width dimensions being greater than said inner width dimension, said inner and outer width dimensions extending in a direction generally parallel with the plane in which said tissue treating member is disposed; said first suction openings being defined by an edge of said electrode and an edge of a portion of said support element comprising insulating material; and said second suction openings being wholly defined by said electrode.

21. The tool of claim 20, wherein said first strip has said inner and outer width dimensions, and said second strip has an inner width dimension located adjacent said intersecting area and a pair of outer width dimensions spaced from said inner width dimension of said second strip and located on opposite sides of said intersecting area, said outer width dimensions of said second strip being greater than said inner width dimension of said second strip, and said inner and outer width dimensions of said second strip extending in a direction generally parallel with the plane in which said tissue treating member is disposed.

22. The tool of claim 20, wherein each said suction opening is wholly defined by said tissue treating member of said electrode.

23. The tool of claim 20, wherein one of said suction openings has an outer edge defined by an edge of said support element and disposed in opposed relation with said inner edge of said one suction opening.

* * * * *

UNITED STATES PATENT AND TRADEMARK OFFICE
CERTIFICATE OF CORRECTION

PATENT NO. : 8,845,576 B2  
APPLICATION NO. : 12/653841  
DATED : September 30, 2014  
INVENTOR(S) : Steven C. Kramer et al.

Page 1 of 2

It is certified that error appears in the above-identified patent and that said Letters Patent is hereby corrected as shown below:

Delete Title Page and replace with new Title Page. (Attached)

In the Claims

Column 13, line 64, Claim 18; after "edge" insert --of--.

Cancel Claim 19.

Cancel Claim 22.

Cancel Claim 23.

Signed and Sealed this
Seventeenth Day of February, 2015

Michelle K. Lee
*Deputy Director of the United States Patent and Trademark Office*

(12) United States Patent
Kramer et al.

(10) Patent No.: US 8,845,576 B2
(45) Date of Patent: Sep. 30, 2014

(54) ELECTROSURGICAL TOOL

(75) Inventors: Steven C. Kramer, San Jose, CA (US); Andrew J. Hamel, San Mateo, CA (US); Reid Cover, Mountain View, CA (US)

(73) Assignee: Stryker Corporation, Kalamazoo, MI (US)

(*) Notice: Subject to any disclaimer, the term of this patent is extended or adjusted under 35 U.S.C. 154(b) by 778 days.

(21) Appl. No.: 12/653,841

(22) Filed: Dec. 18, 2009

(65) Prior Publication Data
US 2010/0160910 A1 Jun. 24, 2010

Related U.S. Application Data

(60) Provisional application No. 61/203,472, filed on Dec. 23, 2008.

(51) Int. Cl.
| | |
|---|---|
| A61M 1/00 | (2006.01) |
| A61B 18/14 | (2006.01) |
| A61B 18/18 | (2006.01) |
| A61F 7/12 | (2006.01) |
| A61B 18/00 | (2006.01) |
| A61B 17/00 | (2006.01) |
| A61B 18/16 | (2006.01) |

(52) U.S. Cl.
CPC .... *A61B 18/1482* (2013.01); *A61B 2018/00601* (2013.01); *A61B 2017/00973* (2013.01); *A61B 2018/00577* (2013.01); *A61B 18/16* (2013.01); *A61B 2218/007* (2013.01)
USPC ............................. 604/35; 606/41; 607/113

(58) Field of Classification Search
USPC ................... 604/35, 114; 606/32, 41, 45–50; 607/99, 105, 113
See application file for complete search history.

(56) References Cited

U.S. PATENT DOCUMENTS

| | | |
|---|---|---|
| 3,974,833 A | 8/1976 | Durden, III |
| 5,290,282 A | 3/1994 | Casscells |
| 5,324,254 A | 6/1994 | Phillips |
| 5,395,312 A | 3/1995 | Desai |
| 5,401,274 A | 3/1995 | Kusunoki |
| 5,520,685 A | 5/1996 | Wojciechowicz |
| 5,697,281 A | 12/1997 | Eggers et al. |
| 5,697,536 A | 12/1997 | Eggers et al. |
| 5,730,742 A | 3/1998 | Wojciechowicz |
| 5,810,806 A | 9/1998 | Ritchart et al. |
| 5,830,214 A | 11/1998 | Flom et al. |
| 5,833,689 A | 11/1998 | Long |

(Continued)

OTHER PUBLICATIONS

Stryker 90-ASD Probe discussed in paragraphs [0004] and [0005] of US 2006/0235377 A1 (date unknown), 2 pages.

(Continued)

*Primary Examiner* — Linda Dvorak
*Assistant Examiner* — Brian M Antiskay
(74) *Attorney, Agent, or Firm* — Flynn, Thiel, Boutell & Tanis, P.C.

(57) ABSTRACT

An electrosurgical tool for cauterizing or ablating patient tissue, which tool includes a tubular shaft which defines therein a conduit in communication with a suction source and which mounts an electrode at the distal end thereof. An electrode support element is provided at the distal end of the shaft for mounting and insulating the electrode. The support element and the electrode together define a suction opening at the treating surface of the electrode which minimizes clogging of the tool.

20 Claims, 10 Drawing Sheets